US010513526B2

(12) United States Patent
Ben-David et al.

(10) Patent No.: US 10,513,526 B2
(45) Date of Patent: Dec. 24, 2019

(54) SOLID STATE FORMS OF SPIRO-OXINDOLE COMPOUNDS

(71) Applicant: Xenon Pharmaceuticals Inc., Burnaby (CA)

(72) Inventors: Ronen Ben-David, Netanya (IL); Stephen Bierlmaier, Thorndale, PA (US); Ralph Curtis Haltiwanger, West Chester, PA (US); Alexandr Jegorov, Dobra Voda (CZ); Raeann Ruiyun Wu, Montville, NJ (US); Mehran Yazdanian, Philadelphia, PA (US)

(73) Assignee: Xenon Pharmaceuticals Inc., Burnaby (CA)

( * ) Notice: Subject to any disclaimer, the term of this patent is extended or adjusted under 35 U.S.C. 154(b) by 0 days.

(21) Appl. No.: 16/156,718

(22) Filed: Oct. 10, 2018

(65) Prior Publication Data

US 2019/0071449 A1    Mar. 7, 2019

Related U.S. Application Data

(62) Division of application No. 15/625,724, filed on Jun. 16, 2017, now Pat. No. 10,118,932.

(60) Provisional application No. 62/351,150, filed on Jun. 16, 2016.

(51) Int. Cl.
*C07D 491/20* (2006.01)
*A61K 31/407* (2006.01)

(52) U.S. Cl.
CPC .......... *C07D 491/20* (2013.01); *A61K 31/407* (2013.01); *C07B 2200/13* (2013.01)

(58) Field of Classification Search
CPC .................... C07D 491/20; A61K 31/407
See application file for complete search history.

(56) References Cited

U.S. PATENT DOCUMENTS

| 7,700,641 | B2 | 4/2010 | Chafeev et al. |
| 7,935,721 | B2 | 5/2011 | Sun et al. |
| 8,106,087 | B2 | 1/2012 | Chafeev et al. |
| 8,445,696 | B2 | 5/2013 | Cadieux et al. |
| 8,450,358 | B2 | 5/2013 | Chafeev et al. |
| 8,742,109 | B2 | 6/2014 | Cadieux et al. |
| 8,883,840 | B2 | 11/2014 | Chafeev et al. |
| 9,260,446 | B2 | 2/2016 | Cadieux et al. |
| 9,480,677 | B2 | 11/2016 | Chafeev et al. |
| 9,487,535 | B2 | 11/2016 | Sun et al. |
| 9,504,671 | B2 | 11/2016 | Winters et al. |
| 9,695,185 | B2 | 7/2017 | Cadieux et al. |
| 2017/0066777 | A1 | 3/2017 | Sun et al. |
| 2017/0073351 | A1 | 3/2017 | Chafeev et al. |
| 2017/0095449 | A1 | 4/2017 | Winters et al. |
| 2018/0016283 | A1 | 1/2018 | Ben-David et al. |

FOREIGN PATENT DOCUMENTS

| WO | WO 2006/110917 A2 | 10/2006 |
| WO | WO 2010/045197 A1 | 4/2010 |
| WO | WO 2010/045251 A2 | 4/2010 |
| WO | WO 2011/002708 A1 | 1/2011 |
| WO | WO 2011/047174 A1 | 4/2011 |
| WO | WO 2011/106729 A2 | 9/2011 |
| WO | WO 2013/154712 A1 | 10/2013 |
| WO | WO 2017/218957 A1 | 12/2017 |

OTHER PUBLICATIONS

U.S. Appl. No. 15/604,348, filed May 24, 2017, Cadieux et al.
Caira, "Crystalline Polymorphism of Organic Compounds," *Topics in Current Chemistry* 198:163-208, 1998.
International Search Report and Written Opinion, dated Oct. 6, 2006, for PCTAN PCT/US2006/014352, 11 pages.
International Search Report and Written Opinion, dated Oct. 1, 2010, for PCTAN PCT/US2010/040187, 13 pages.
International Search Report and Written Opinion, dated Apr. 1, 2011, for PCTAN PCT/US2010/052704, 12 pages.
International Search Report and Written Opinion, dated Jun. 9, 2011, for PCTAN PCT/US2011/026359, 14 pages.
International Search Report and Written Opinion, dated Jun. 28, 2013, for PCTAN PCT/US2013/030219, 17 pages.
International Search Report and Written Opinion, dated Oct. 24, 2017, for PCTAN PCT/US2017/037979, 16 pages.

*Primary Examiner* — Karen Cheng
(74) *Attorney, Agent, or Firm* — Cooley LLP; Ivor R. Elrifi; Matthew Pavao

(57) ABSTRACT

The present invention provides solid state forms of certain spiro-oxindole compounds, such as funapide and the racemic mixture of funapide and its corresponding (R) enantiomer, pharmaceutical compositions comprising the solid state forms and processes for preparing the solid state forms and the pharmaceutical compositions.

11 Claims, 14 Drawing Sheets

A characteristic X-ray powder diffractogram of Form $A_0$ of Funapide (TV-45070).

DSC thermograph of Form A₀ of Funapide (XEN-402).

DSC thermograph of Form B₀ of Funapide (TV-45070).

FTIR spectrum by ATR of Form B₀ of Funapide

A characteristic X-ray powder diffractogram of amorphous Funapide (TV-45070).

A DSC thermograph of the amorphous form of Funapide (TV-45070)

X-ray powder diffractograms of the racemic mixture, Form A₀ of Funapide and Form B₀ of Funapide Raman shift spectrums of the racemic mixture, Form A₀ and Form B₀.

SOLID STATE FORMS OF SPIRO-OXINDOLE COMPOUNDS

FIELD OF THE INVENTION

The present invention encompasses solid state forms of certain spiro-oxindole compounds, pharmaceutical compositions comprising the solid state forms and pharmaceutically acceptable excipients, and processes for preparing the solid state forms and the pharmaceutical compositions.

BACKGROUND OF THE INVENTION

PCT Published Patent Application No. WO 2006/110917, PCT Published Patent Application No. WO 2010/045251, PCT Published Patent Application No. WO 2010/045197, PCT Published Patent Application No. WO 2011/047174, PCT Published Patent Application No. WO 2011/002708, PCT Published Patent Application No. WO 2011/106729 and PCT Published Patent Application No. WO 2013/154712, discloses certain spiro-oxindole compounds, methods of preparing the spiro-oxindole compounds, pharmaceutical compositions comprising the spiro-oxindole compounds and/or methods of using the spiro-oxindole compounds.

One of these spiro-oxindole compounds is funapide, which is also known as TV-45070 or XEN402. Funapide has the following formula (I-S):

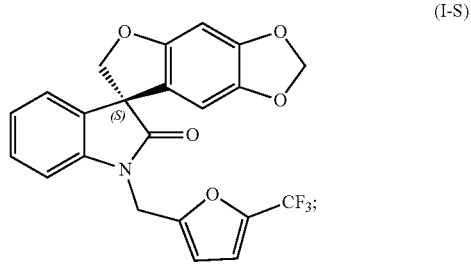

(I-S)

and has the chemical name of (S)-1'-{[5-(trifluoromethyl) furan-2-yl]methyl}spiro[furo[2,3-f][1,3]benzodioxole-7,3'-indol]-2'(1'H)-one.

In particular, PCT Published Patent Application No. WO 2011/002708 specifically discloses funapide and its corresponding (R)-enantiomer; PCT Published Patent Application No. WO 2011/047174 discloses methods of preparing funapide by resolving its racemate by either SMB chromatography or by chiral HPLC; and PCT Published Patent Application No. WO 2013/154712 discloses methods of preparing funapide by asymmetric synthesis.

Funapide is the (S)-enantiomer of the racemic compound previously disclosed in PCT Published Patent Application No. WO 2006/110917 as compound #428 therein. Compound #428 is also known as XEN401.

Funapide and pharmaceutical compositions comprising funapide are useful for the treatment of sodium channel-mediated diseases, preferably diseases related to pain, central nervous conditions such as epilepsy, anxiety, depression and bipolar disease; cardiovascular conditions such as arrhythmias, atrial fibrillation and ventricular fibrillation; neuromuscular conditions such as restless leg syndrome; neuroprotection against stroke, neural trauma and multiple sclerosis; and channelopathies such as erythromelalgia and familial rectal pain syndrome.

The relevant disclosures of the above published patent applications are incorporated in full by reference herein.

Polymorphism, the occurrence of different crystalline forms of the same molecule, is a property of some molecules and molecular complexes. A single molecule may give rise to a variety of polymorphs having distinct crystal structures and physical properties such as melting point, thermal behaviors (e.g., measured by differential scanning calorimetry—"DSC" or thermogravimetric analysis—"TGA"), X-ray diffraction pattern, infrared absorption fingerprint, and solid state ($^{13}C$—) NMR spectrum. One or more of these techniques may be used to distinguish different polymorphic forms of a compound.

Different solid state forms (including solvated forms) of an active pharmaceutical ingredient may possess different properties. Such variations in the properties of different solid state forms and solvates may provide a basis for improving formulation, for example, by facilitating better processing or handling characteristics, changing the dissolution profile in a favorable direction, or improving stability (polymorphic as well as chemical stability) and shelf-life. These variations in the properties of different solid state forms may also offer improvements to the final dosage form, for instance, if they serve to improve bioavailability. Different solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life (chemical/physical stability). For at least these reasons, there is a need for solid state forms (including solvated forms) of funapide.

SUMMARY OF THE INVENTION

The present invention provides solid state forms of certain spiro-oxindole compounds, preferably funapide or the racemic mixture, as disclosed herein, and pharmaceutical compositions thereof.

The present invention also encompasses the use of any one of solid state forms of certain spiro-oxindole compounds, preferably funapide or the racemic mixture, as disclosed herein, for the preparation of pharmaceutical compositions of the spiro-oxindole compounds.

The present invention also provides methods of preparing the solid state forms of certain spiro-oxindole compounds, preferably funapide or the racemic mixture, as disclosed herein.

The present invention also provides a process for preparing the above-mentioned pharmaceutical compositions. The process comprises combining any one of the solid state forms of certain spiro-oxindole compounds, preferably funapide or the racemic mixture, as disclosed herein, with at least one pharmaceutically acceptable excipient.

The solid state forms and the pharmaceutical compositions of certain spiro-oxindole compounds, preferably funapide or the racemic mixture, can be used as medicaments, particularly for the treatment of sodium channel-mediated diseases and conditions, such as pain.

The present invention also provides a method of treating sodium channel-mediated diseases and conditions, such as pain, comprising administering a therapeutically effective amount of any one of the solid state forms of certain spiro-oxindole compounds, preferably funapide or the racemic mixture, as disclosed herein, or at least one of the above pharmaceutical compositions, to a subject suffering from sodium channel-mediated diseases and conditions, such as pain, or otherwise in need of the treatment.

DETAILED DESCRIPTION OF THE INVENTION

Figure 1:
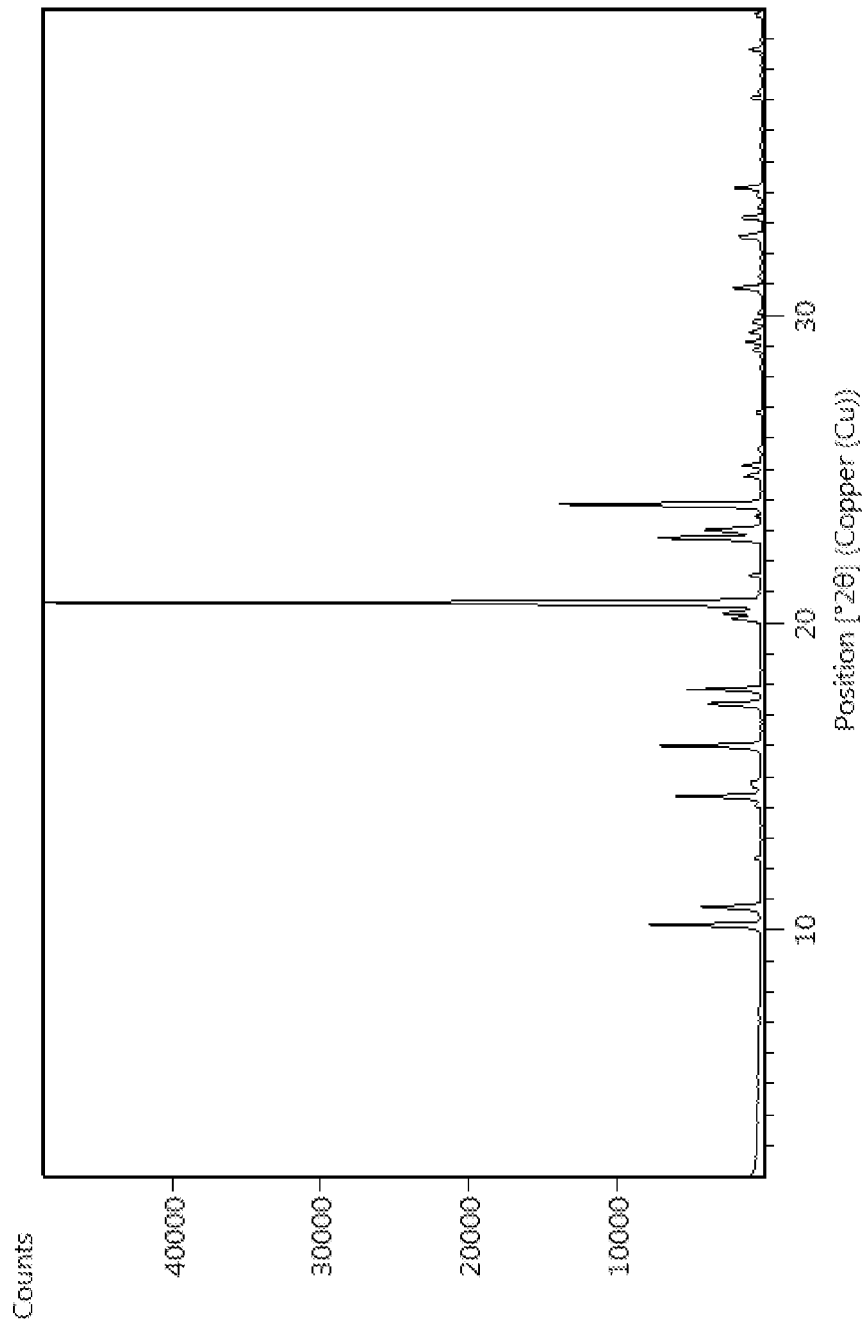
FIG. 1 shows a characteristic X-ray powder diffractogram of Form $A_0$ of funapide (TV-45070).

The present invention encompasses solid state forms of certain spiro-oxindole compounds, preferably funapide or a racemic mixture of funapide and its corresponding (R)-enantiomer. Solid state properties of funapide or the racemic mixture can be influenced by controlling the conditions under which funapide or the racemic mixture is obtained in solid form.

As used herein, "solid state forms of certain spiro-oxindole compounds" is intended to include the crystalline forms of funapide, the amorphous form of funapide, and the crystalline form of the racemic mixture comprising funapide and its corresponding (R)-enantiomer, as described herein.

In some embodiments, the crystalline forms of funapide of the invention are substantially free of any other forms of funapide, or of specified polymorphic forms of funapide, respectively.

As used herein, "substantially free" when referring to a solid state form of the funapide is intended to mean that the solid state form of the present invention contains 20% (w/w) or less of any other polymorphs, or of specified polymorph of funapide, or the amorphous form of funapide. According to some embodiments, a solid state form of funapide contains 10% (w/w) or less, 5% (w/w) or less, 2% (w/w) or less, 1% (w/w) or less, 0.5% (w/w) or less, or 0.2% (w/w) or less of any other polymorphs, or of specified polymorph of funapide or the amorphous form of funapide. In other embodiments, a solid state form of funapide of the present invention contains from 1% to 20% (w/w), from 5% to 20% (w/w), or from 5% to 10% (w/w) of any other solid state form or of a specified polymorph of funapide or of the amorphous form of funapide.

Depending on with which other solid state form a comparison is made, the crystalline forms of funapide of the present invention have advantageous properties selected from at least one of the following: chemical purity, flowability, solubility, dissolution rate, morphology or crystal habit, stability—such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility, and bulk density.

Particularly, it has been found that the crystalline forms of funapide of the present invention are highly soluble in numerous solvents such as acetone, acetonitrile, ethyl acetate, isopropyl acetate, methyl tert-butyl ether, tetrahydrofuran and toluene. The crystalline forms of funapide of the present invention also demonstrate good physical stability.

As used herein, the term "highly soluble" in reference to solid state forms of funapide of the present invention corresponds to a solid state form of funapide having a solubility of above 100 mg/mL at room temperature.

A solid state form, such as a crystalline form or an amorphous form, may be referred to herein as being characterized by graphical data "as depicted in" or "as substantially depicted in" a Figure. Such data include, for example, powder X-ray diffractograms, DSC thermographs, FTIR spectrums by ATR and Raman shift spectrums. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystalline form and confirm whether the two sets of graphical data are characterizing the same crystal form or two different crystal forms. A crystalline form of funapide or the racemic mixture referred to herein as being characterized by graphical data "as depicted in" or "as substantially depicted in" a Figure will thus be understood to include any crystalline forms of funapide or the racemic mixture characterized with the graphical data having such small variations, as are well known to the skilled person, in comparison with the Figure.

As used herein, the term "isolated" in reference to solid state forms of funapide or the racemic mixture of the present invention corresponds to a solid state form of funapide or the racemic mixture that is physically separated from the reaction mixture in which it is formed.

As used herein, unless stated otherwise, the XRPD measurements are taken using copper Kα radiation at 45 kV and 40 mA.

As used herein, unless stated otherwise, the DSC measurements were measured with a heat ramp of 10° C./min.

When an object or a mixture, such as a solid state form of funapide or the racemic mixture or a reaction mixture or solution, is characterized herein as being at or allowed to come to "room temperature" or "ambient temperature" (often abbreviated as "RT"), it is intended to mean that the temperature of the object or mixture is close to, or the same as, that of the space, e.g., the room or fume hood, in which the object or mixture is located. Typically, room temperature is from about 20° C. to about 30° C., or about 22° C. to about 27° C., or about 25° C.

The amount of solvent employed in a chemical process, e.g., a reaction or a crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours. As used herein, the term "reduced pressure" refers to a pressure that is less than atmospheric pressure. For example, reduced pressure is about 10 mbar to about 50 mbar.

As used herein "crystalline form $A_0$ of funapide" or "Form $A_0$" or "Form $A_0$ of funapide" refers to a crystalline form of funapide which may be characterized by X-ray powder diffraction pattern as depicted in FIG. 1.

Figure 5:
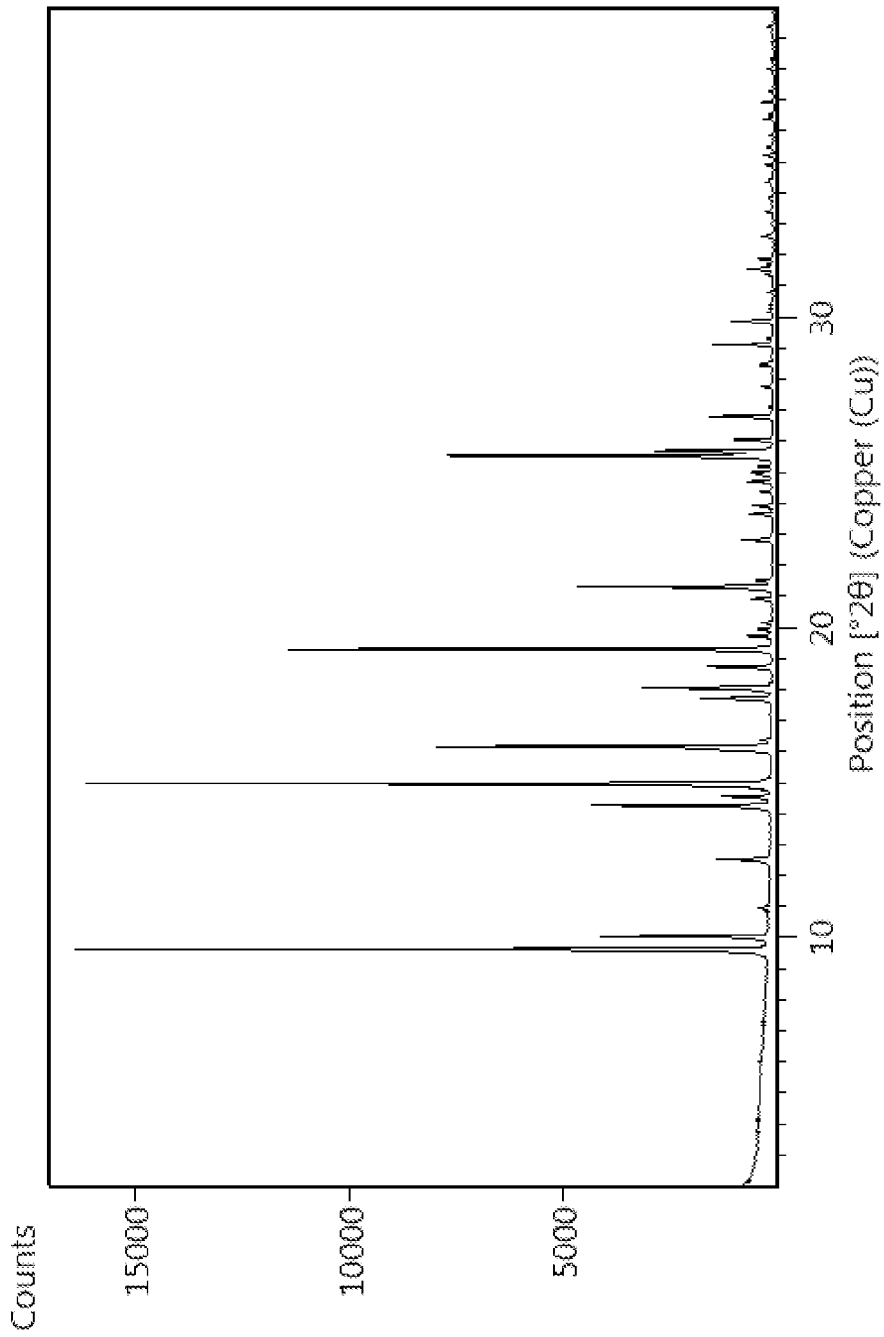
FIG. 5 shows a characteristic X-ray powder diffractogram of Form $B_0$ of funapide (TV-45070).

As used herein "crystalline form $B_0$ of funapide" or "Form $B_0$" or "Form $B_0$ of funapide" refers to a crystalline form of funapide which may be characterized by X-ray powder diffraction pattern as depicted in FIG. 5.

Figure 9:
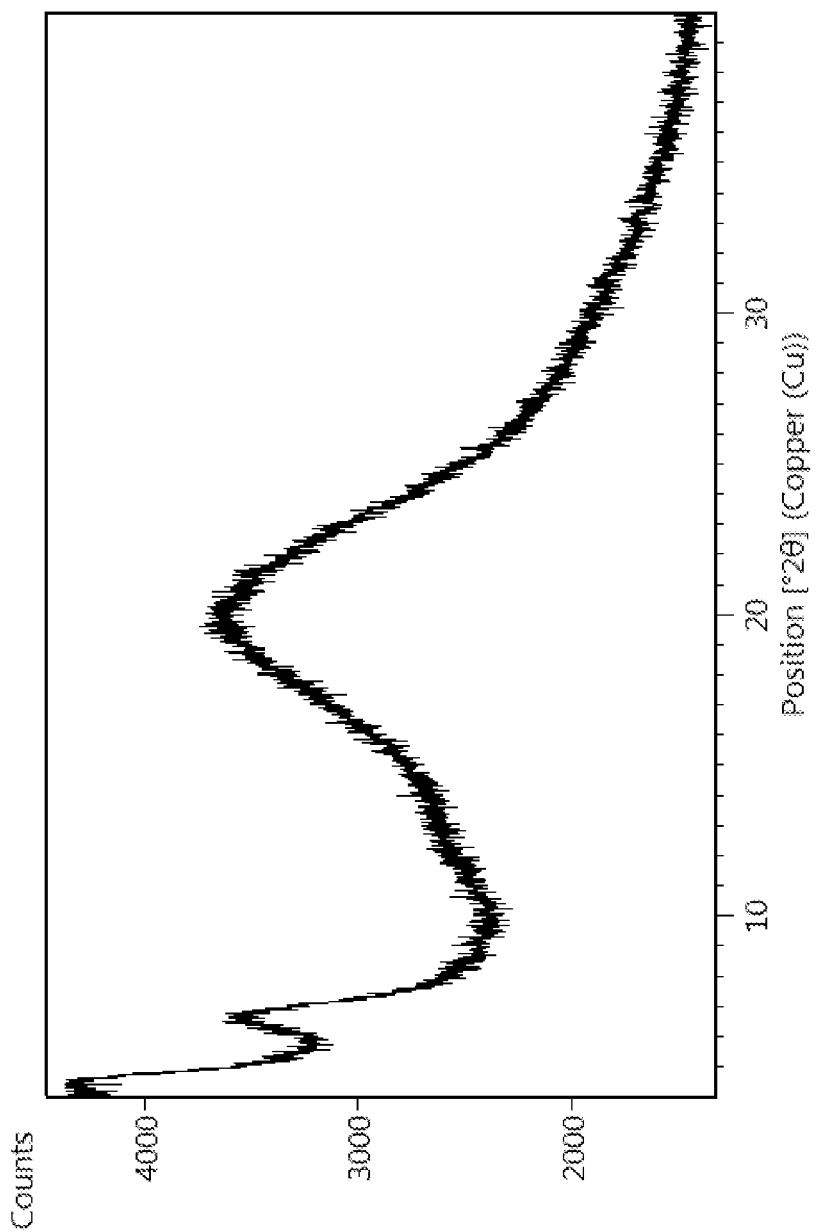
FIG. 9 shows a characteristic X-ray powder diffractogram of amorphous funapide (TV-45070).
Figure 10:
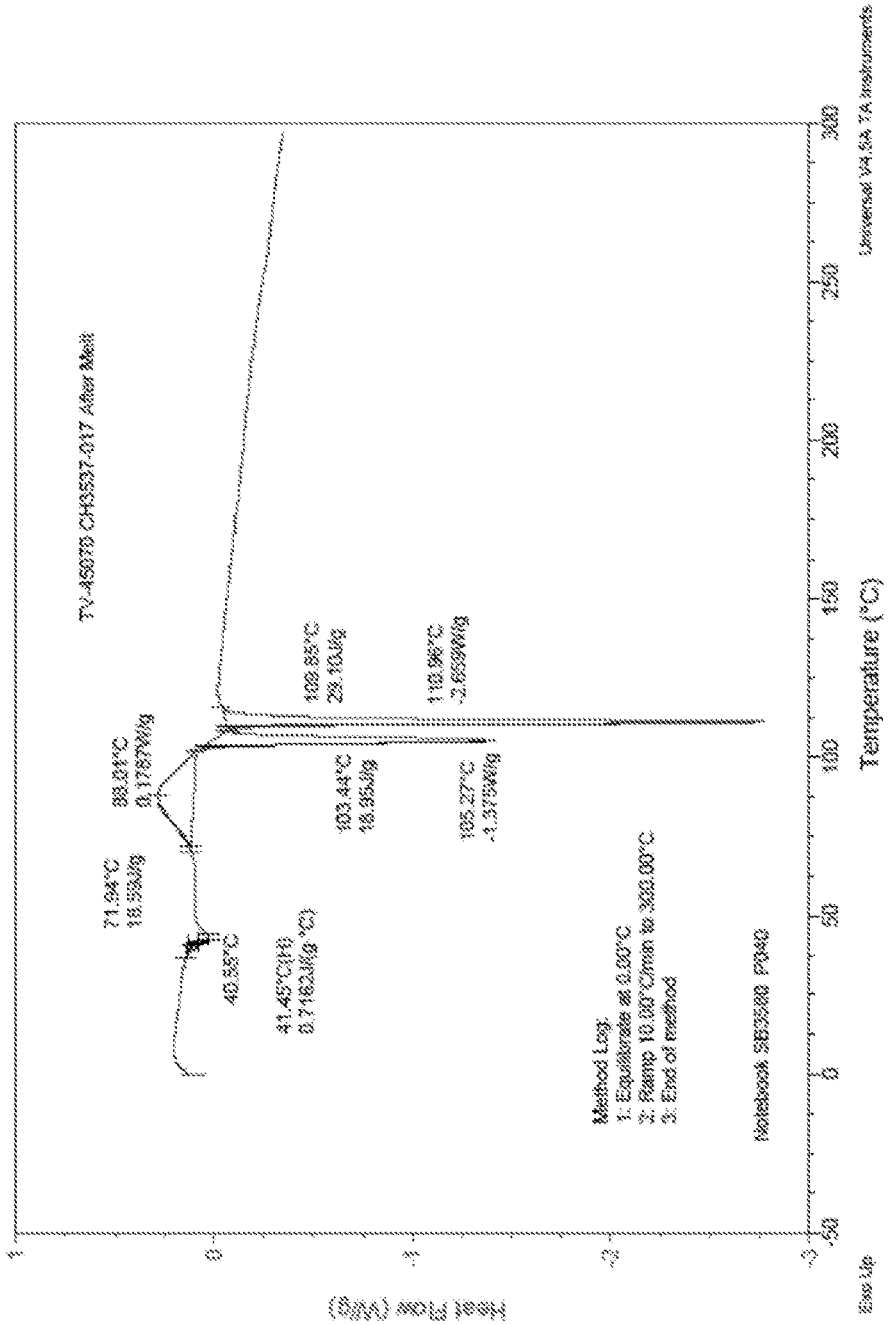
FIG. 10 shows a DSC thermograph of the amorphous form of funapide (TV-45070).

As used herein "amorphous form of funapide" refers to an amorphous form of funapide which may be characterized by X-ray powder diffraction pattern as depicted in FIG. 9 and further by a DSC thermograph as depicted in FIG. 10 showing a glass transition at 42° C. and crystallization at 72° C.

Figure 11:
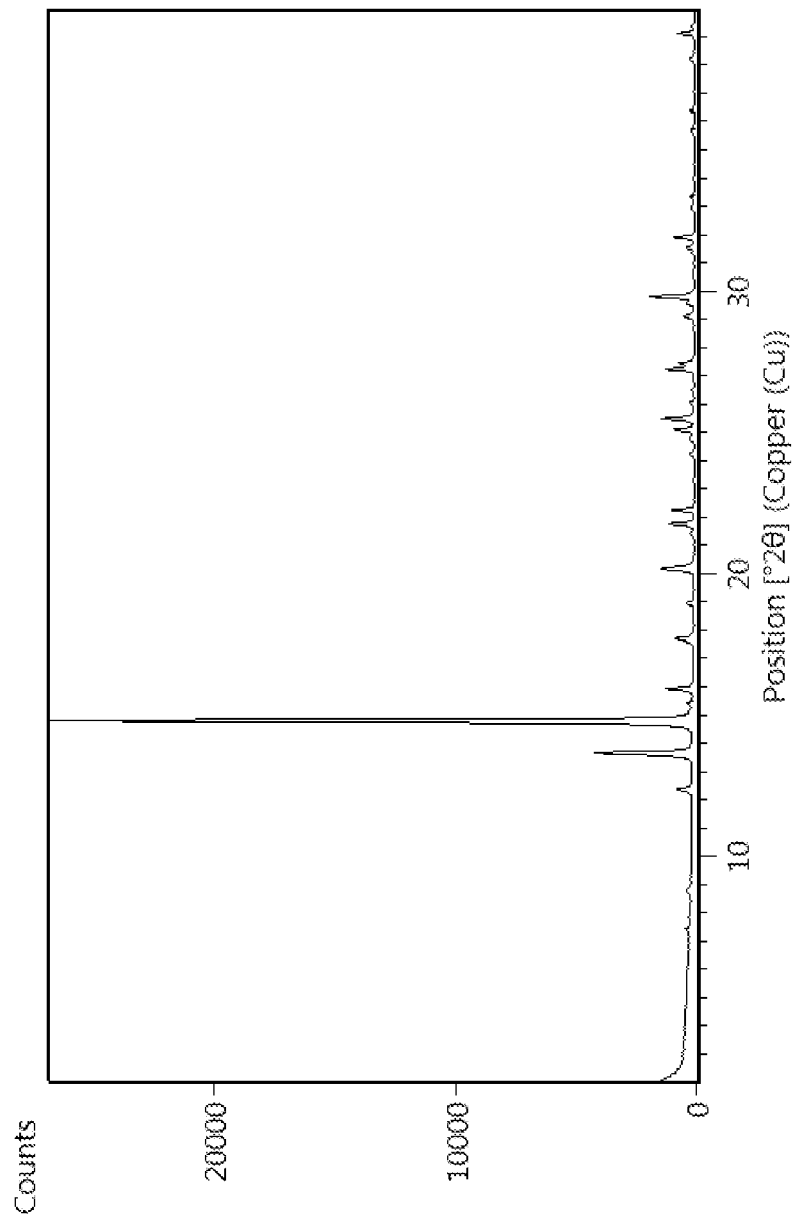
FIG. 11 shows a characteristic X-ray powder diffractogram of the racemic mixture of funapide and its corresponding (R)-enantiomer.

As used herein "the racemic mixture" refers to the crystalline form of the racemic mixture of funapide and its corresponding (R)-enantiomer which may be characterized by an X-ray powder diffraction pattern as depicted in FIG. 11.

In one embodiment, the present invention comprises a crystalline form of funapide, designated herein as crystalline form $A_D$ of funapide, characterized by data selected from one or more of the following: X-ray powder diffraction pattern having peaks at 10.10°, 10.69°, 20.59°, 22.69° and 33.12° θ±0.2° θ; an X-ray powder diffraction pattern as depicted in FIG. 1; and combinations of these data.

Figure 2:
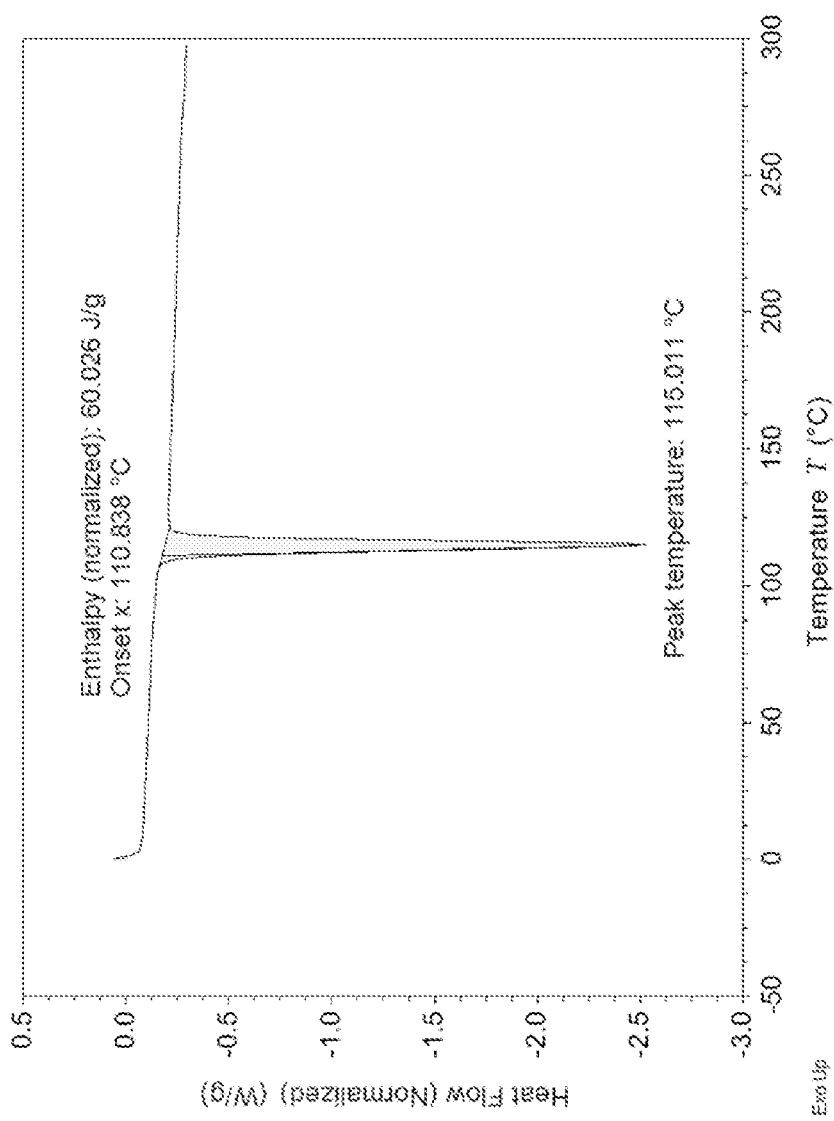
FIG. 2 shows a DSC thermograph of Form $A_0$ of funapide (XEN-402).
Figure 3:
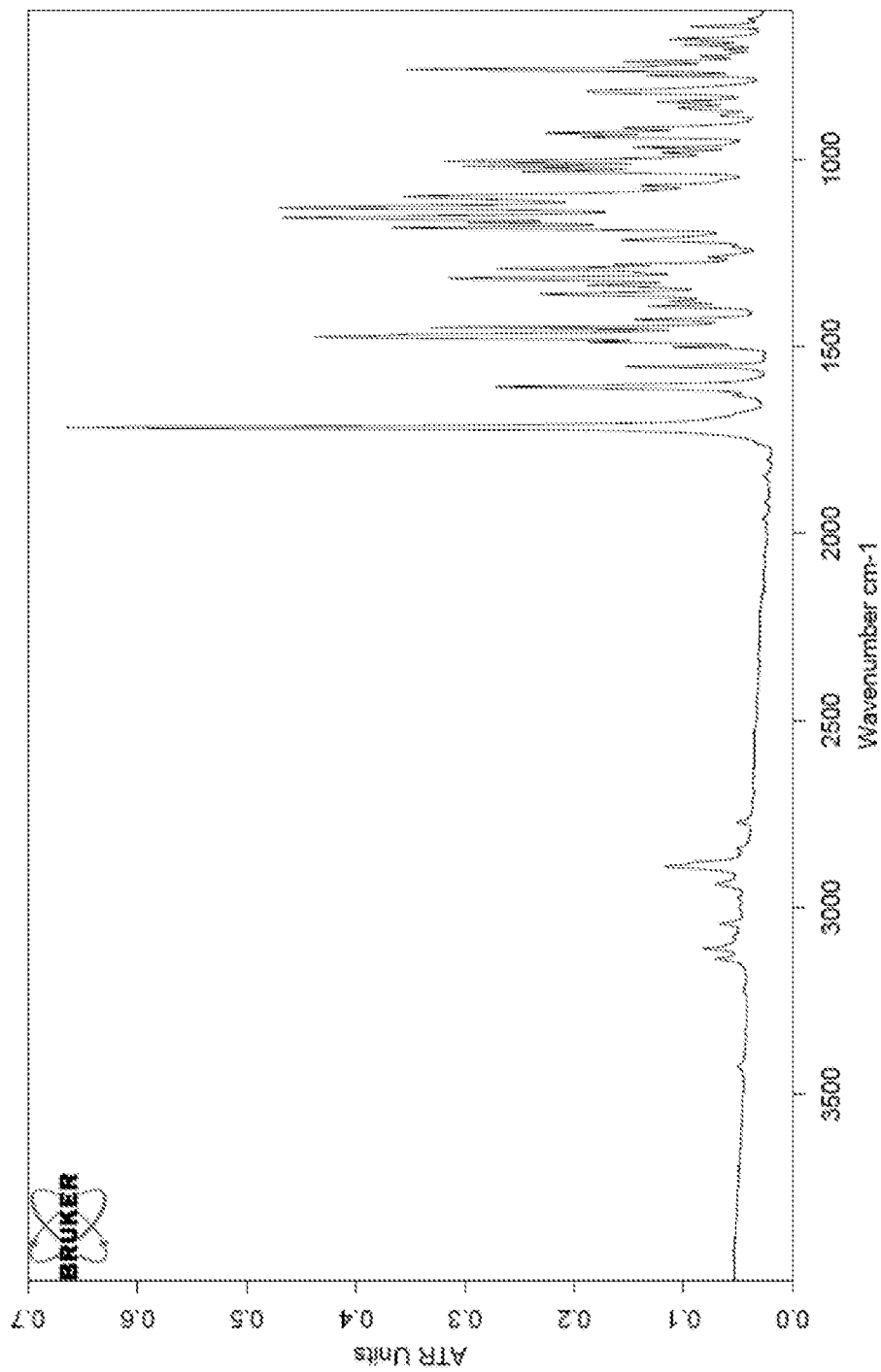
FIG. 3 shows an FTIR spectrum by ATR of Form $A_0$ of funapide.
Figure 4:
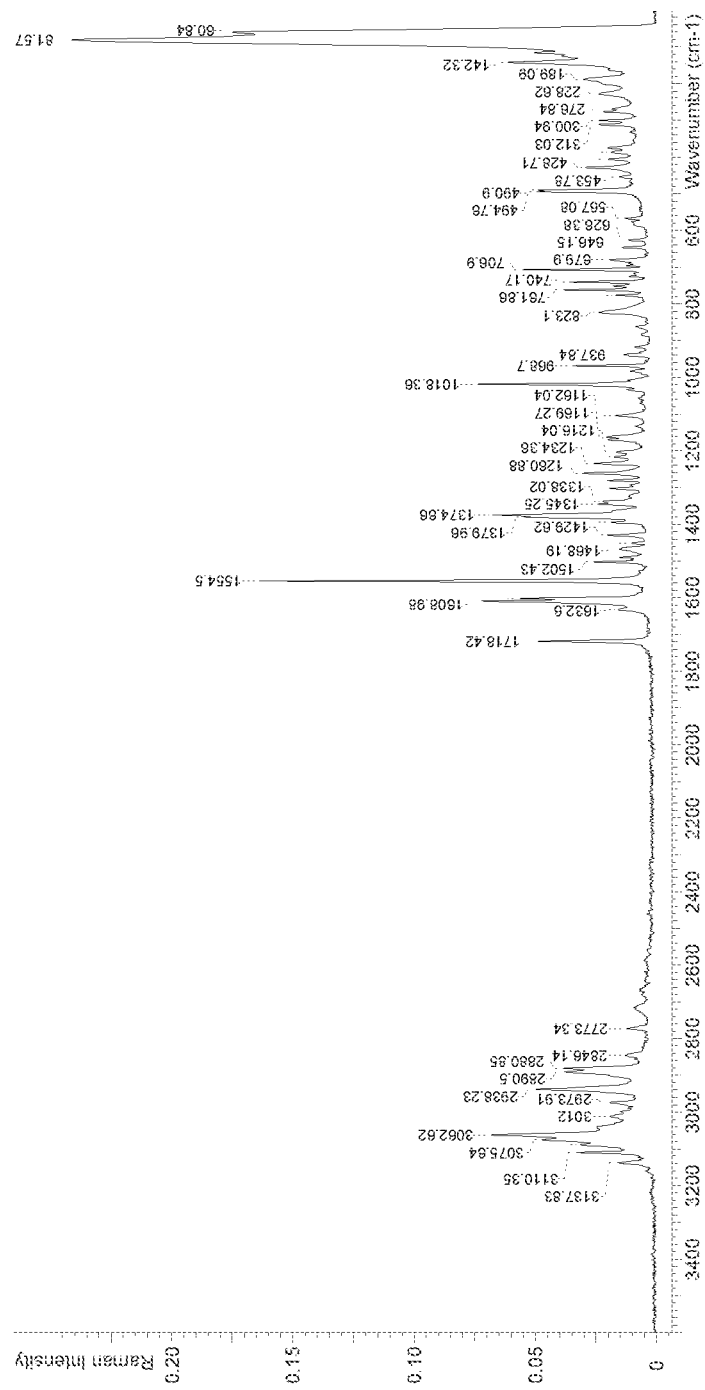
FIG. 4 shows a Raman shift spectrum for Form $A_0$ of funapide.

Crystalline form $A_0$ of funapide may be further characterized by the X-ray powder diffraction pattern having peaks at 10.10°, 10.69°, 20.59°, 22.69° and 33.12° θ±0.2° θ and also having one, two, three or four additional peaks selected from: 15.94°, 17.77°, 20.26°, 23.79°, and 30.84° θ±0.2° θ; a DSC thermogram as depicted in FIG. 2; a 110-116° C. melting point, preferably a 114-116° C. melting point; an FTIR spectrum as depicted in FIG. 3, and a Raman shift spectrum as depicted in FIG. 4.

Crystalline form $A_0$ of funapide may be characterized by each of the above characteristics alone and/or by all possible combinations, e.g., by X-ray powder diffraction pattern having peaks at 10.10°, 10.69°, 20.59°, 22.69° and 33.12° θ±0.2° θ and by an X-ray powder diffraction pattern as depicted in FIG. 1.

In another embodiment, crystalline form $A_0$ of funapide is characterized by one or more of the following Raman shift peaks listed in Table 1:

TABLE 1

| Peak No. | Raman shift (cm$^{-1}$) |
|---|---|
| 1 | 3137.83 |
| 2 | 3110.35 |
| 3 | 3088.66 |
| 4 | 3075.64 |
| 5 | 3062.62 |
| 6 | 3012 |
| 7 | 2973.91 |
| 8 | 2938.23 |
| 9 | 2890.5 |
| 10 | 2880.85 |
| 11 | 2846.14 |
| 12 | 2773.34 |
| 13 | 1718.42 |
| 14 | 1632.6 |
| 15 | 1608.98 |
| 16 | 1601.75 |
| 17 | 1554.5 |
| 18 | 1502.43 |
| 19 | 1489.89 |
| 20 | 1468.19 |
| 21 | 1451.8 |
| 22 | 1429.62 |
| 23 | 1394.43 |
| 24 | 1379.96 |
| 25 | 1374.66 |
| 26 | 1345.25 |
| 27 | 1338.02 |
| 28 | 1302.34 |
| 29 | 1280.64 |
| 30 | 1260.88 |
| 31 | 1234.36 |
| 32 | 1216.04 |
| 33 | 1203.98 |
| 34 | 1169.27 |
| 35 | 1162.04 |
| 36 | 1104.18 |
| 37 | 1018.36 |
| 38 | 968.7 |
| 39 | 937.84 |
| 40 | 823.1 |
| 41 | 776.81 |
| 42 | 761.86 |

TABLE 1-continued

| Peak No. | Raman shift (cm$^{-1}$) |
|---|---|
| 43 | 751.26 |
| 44 | 740.17 |
| 45 | 706.9 |
| 46 | 679.9 |
| 47 | 646.15 |
| 48 | 626.38 |
| 49 | 567.08 |
| 50 | 494.76 |
| 51 | 490.9 |
| 52 | 453.78 |
| 53 | 428.71 |
| 54 | 406.53 |
| 55 | 386.76 |
| 56 | 375.19 |
| 57 | 312.03 |
| 58 | 300.94 |
| 59 | 276.84 |
| 60 | 228.62 |
| 61 | 189.09 |
| 62 | 142.32 |
| 63 | 116.28 |
| 64 | 81.57 |
| 65 | 60.84 |

In another embodiment, the present invention comprises crystalline form of funapide, designated herein as crystalline form $B_0$ of funapide, characterized by data selected from one or more of the following: X-ray powder diffraction pattern having peaks at 9.61°, 10.03°, 14.95°, 19.28°, and 21.30° θ±0.2° θ; an X-ray powder diffraction pattern as depicted in FIG. 5; and combinations of these data.

Figure 6:
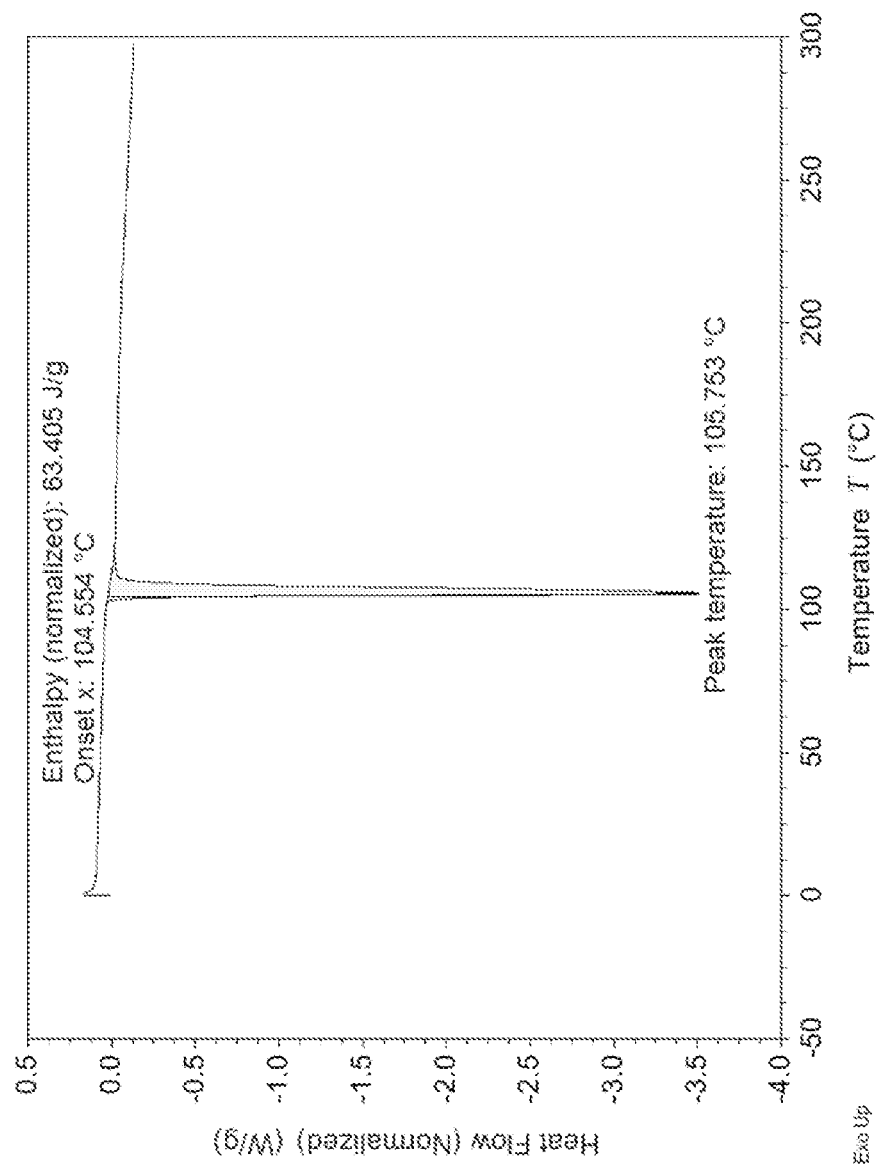
FIG. 6 shows a DSC thermograph of Form $B_0$ of funapide (TV-45070).
Figure 7:
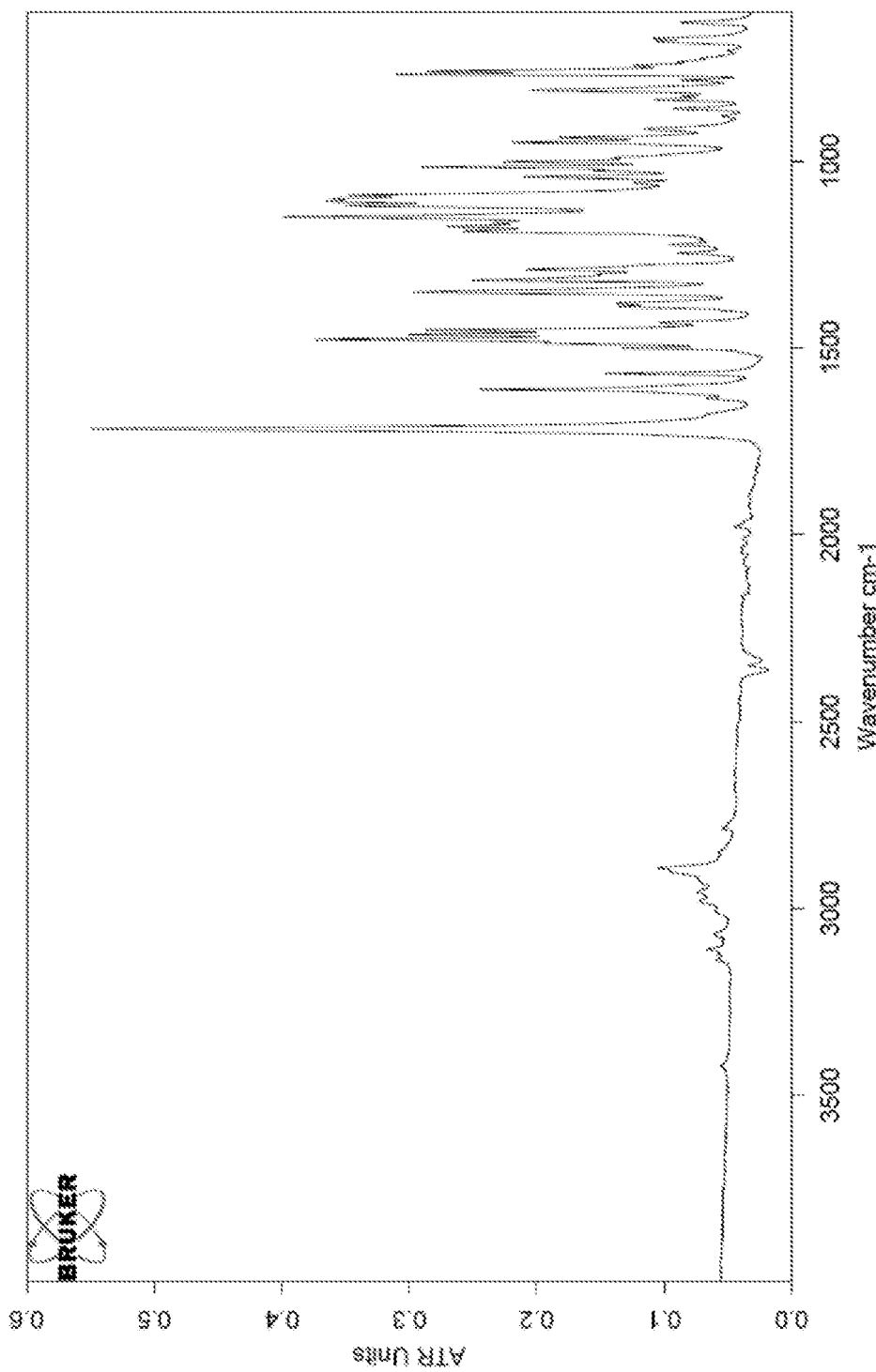
FIG. 7 shows an FTIR spectrum by ATR of Form $B_0$ of funapide.
Figure 8:
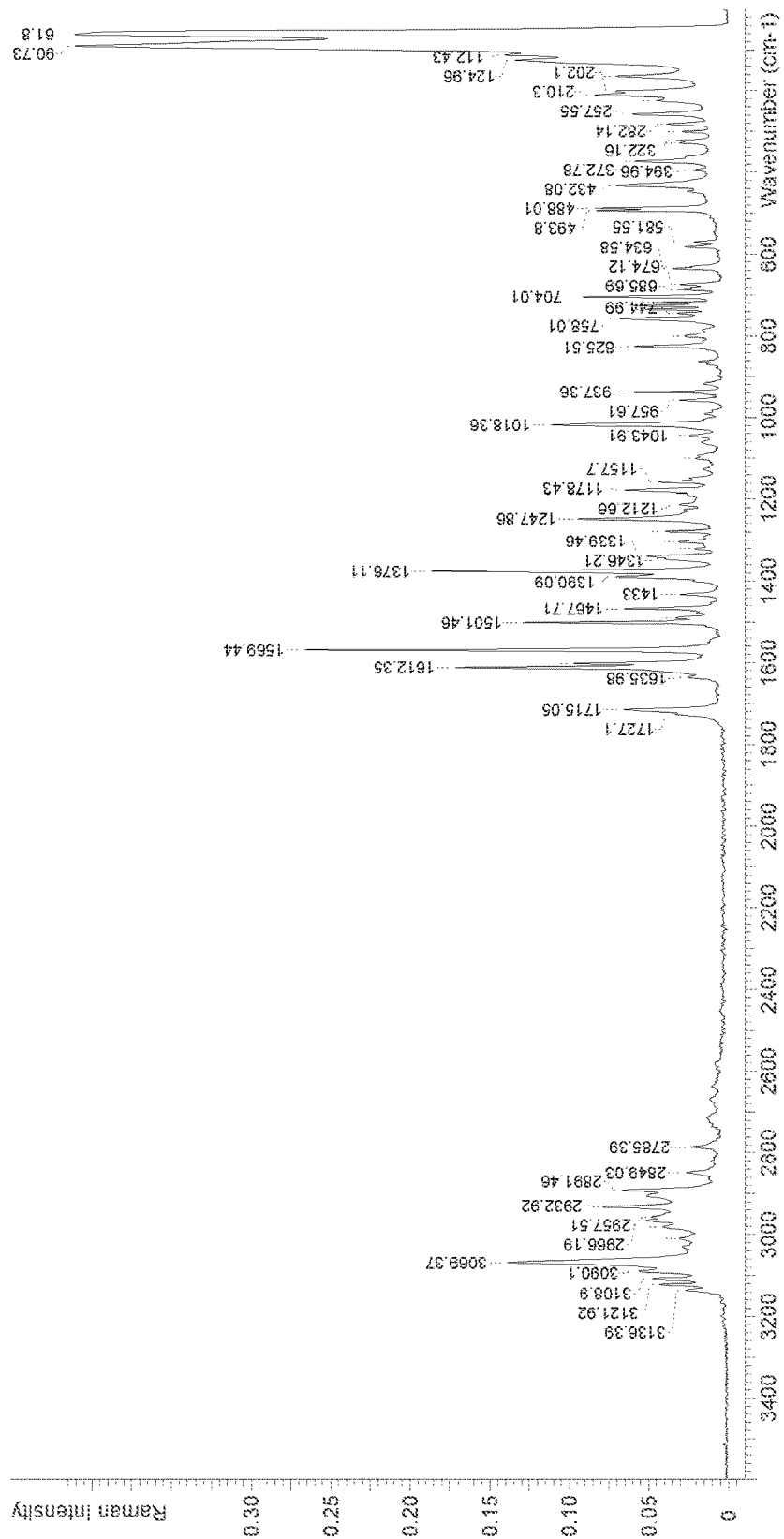
FIG. 8 shows a Raman shift spectrum for Form $B_0$ of funapide.

Crystalline form $B_0$ of funapide may be further characterized by the X-ray powder diffraction pattern having peaks at 9.61°, 10.03°, 14.95°, 19.28°, and 21.30° θ±0.2° θ and also having one, two, three or four additional peaks selected from: 12.51°, 16.14°, 18.03°, 18.72°, and 25.50° θ±0.2° θ; a DSC thermogram as depicted in FIG. 6 showing a 104-107° C. melting point; an FTIR spectrum as depicted in FIG. 7 and a Raman shift spectrum as depicted in FIG. 8.

Crystalline form $B_0$ of funapide may be characterized by each of the above characteristics alone and/or by all possible combinations, e.g. by X-ray powder diffraction pattern as having peaks at 9.61°, 10.03°, 14.95°, 19.28°, and 21.30° θ±0.2° θ and by an X-ray powder diffraction pattern as depicted in FIG. 5.

In another embodiment, crystalline form $B_0$ of funapide is characterized by one or more of the following Raman shift peaks listed in Table 2:

TABLE 2

| Peak No. | Raman shift (cm$^{-1}$) |
|---|---|
| 1 | 3136.39 |
| 2 | 3121.92 |
| 3 | 3108.9 |
| 4 | 3090.1 |
| 5 | 3069.37 |
| 6 | 3029.35 |
| 7 | 3010.07 |
| 8 | 2981.14 |
| 9 | 2966.19 |
| 10 | 2957.51 |
| 11 | 2932.92 |
| 12 | 2905.93 |
| 13 | 2891.46 |
| 14 | 2849.03 |
| 15 | 2785.39 |
| 16 | 1727.1 |
| 17 | 1715.05 |
| 18 | 1635.98 |
| 19 | 1612.35 |
| 20 | 1601.75 |
| 21 | 1569.44 |
| 22 | 1501.46 |
| 23 | 1490.37 |
| 24 | 1467.71 |
| 25 | 1433 |
| 26 | 1390.09 |
| 27 | 1376.11 |
| 28 | 1346.21 |
| 29 | 1339.46 |
| 30 | 1321.14 |
| 31 | 1303.3 |
| 32 | 1278.23 |
| 33 | 1247.86 |
| 34 | 1212.66 |
| 35 | 1178.43 |
| 36 | 1157.7 |
| 37 | 1100.32 |
| 38 | 1043.91 |
| 39 | 1018.36 |
| 40 | 957.61 |
| 41 | 937.36 |
| 42 | 825.51 |
| 43 | 799.95 |
| 44 | 758.01 |
| 45 | 744.99 |
| 46 | 734.86 |
| 47 | 726.19 |
| 48 | 718.95 |
| 49 | 704.01 |
| 50 | 685.69 |
| 51 | 674.12 |
| 52 | 634.58 |
| 53 | 581.55 |
| 54 | 569.49 |
| 55 | 493.8 |
| 56 | 488.01 |
| 57 | 432.08 |
| 58 | 394.96 |
| 59 | 372.78 |
| 60 | 327.94 |
| 61 | 322.16 |
| 62 | 300.46 |
| 63 | 282.14 |
| 64 | 257.55 |
| 65 | 224.28 |
| 66 | 210.3 |
| 67 | 202.1 |
| 68 | 164.98 |
| 69 | 124.96 |
| 70 | 112.43 |
| 71 | 90.73 |
| 72 | 61.8 |

In one embodiment, the present invention comprises a crystalline form of the racemic mixture of funapide and its corresponding (R)-enantiomer, designated herein as the crystalline form of the racemic mixture, characterized by data selected from one or more of the following: X-ray powder diffraction pattern having peaks at 13.68°, 14.83°, 20.17°, 25.49° and 29.80° θ±0.2° θ; an X-ray powder diffraction pattern as depicted in FIG. 11; and combinations of these data.

Figure 12:
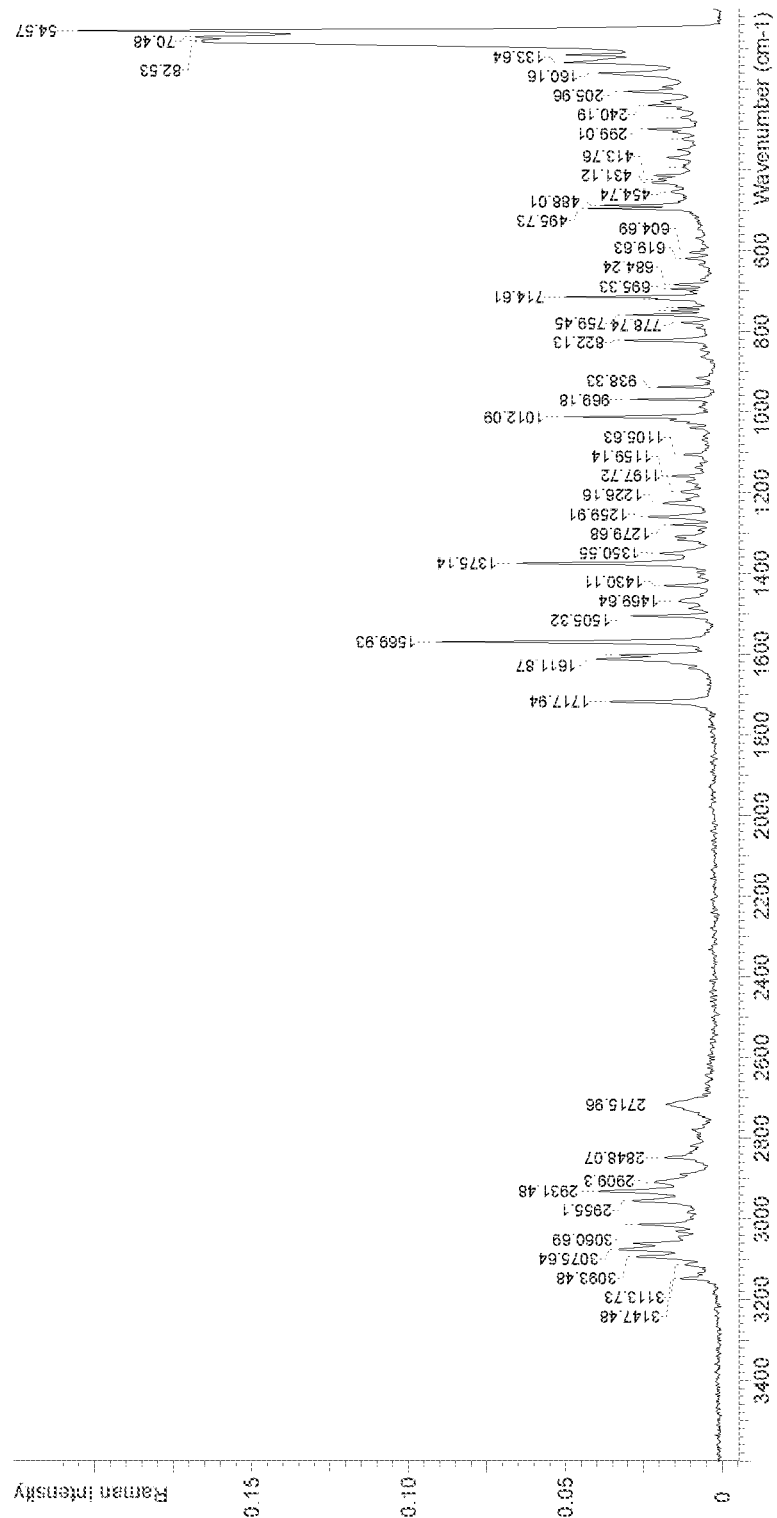
FIG. 12 shows a Raman shift spectrum for the racemic mixture of funapide and its corresponding (R)-enantiomer.

The crystalline form of the racemic mixture may be further characterized by the X-ray powder diffraction pattern having peaks at 13.68°, 14.83°, 20.17°, 25.49° and 29.80° θ±0.2° θ and also having one, two, three or four additional peaks selected from: 15.94°, 22.24°, 27.21°, and 31.91° θ±0.2° θ; and a Raman shift spectrum as depicted in FIG. 12.

In another embodiment, the racemic mixture is characterized by one or more of the XRPD peaks listed in Table 3:

TABLE 3

| Pos. [°2θ] | d-spacing [Å] | Rel. Int. [%] |
|---|---|---|
| 12.38 | 7.15 | 3 |
| 13.68 | 6.47 | 17 |
| 14.83 | 5.97 | 100 |
| 15.94 | 5.56 | 5 |
| 17.74 | 5.00 | 3 |
| 18.98 | 4.67 | 2 |
| 20.17 | 4.40 | 6 |
| 21.78 | 4.08 | 4 |
| 22.24 | 3.99 | 4 |
| 25.07 | 3.55 | 3 |
| 25.11 | 3.54 | 3 |
| 25.49 | 3.49 | 6 |
| 27.21 | 3.27 | 5 |
| 27.45 | 3.25 | 3 |
| 29.13 | 3.06 | 2 |
| 29.58 | 3.02 | 1 |
| 29.80 | 3.00 | 8 |
| 31.54 | 2.83 | 2 |
| 31.91 | 2.80 | 4 |
| 39.12 | 2.30 | 3 |

In another embodiment, the crystalline form of the racemic mixture is characterized by one or more of the following Raman shift peaks listed in Table 4:

TABLE 4

| Peak No. | Raman shift (cm$^{-1}$) |
|---|---|
| 1 | 3147.48 |
| 2 | 3113.73 |
| 3 | 3093.48 |
| 4 | 3075.64 |
| 5 | 3060.69 |
| 6 | 3013.92 |
| 7 | 2984.03 |
| 8 | 2955.1 |
| 9 | 2931.48 |
| 10 | 2909.3 |
| 11 | 2848.07 |
| 12 | 2715.96 |
| 13 | 1717.94 |
| 14 | 1611.87 |
| 15 | 1602.71 |
| 16 | 1569.93 |
| 17 | 1505.32 |
| 18 | 1487 |
| 19 | 1469.64 |
| 20 | 1430.11 |
| 21 | 1375.14 |
| 22 | 1350.55 |
| 23 | 1308.61 |
| 24 | 1279.68 |
| 25 | 1259.91 |
| 26 | 1226.16 |
| 27 | 1197.72 |
| 28 | 1159.14 |
| 29 | 1105.63 |
| 30 | 1012.09 |
| 31 | 969.18 |
| 32 | 938.33 |
| 33 | 822.13 |
| 34 | 778.74 |
| 35 | 759.45 |
| 36 | 749.33 |
| 37 | 741.61 |
| 38 | 720.4 |
| 39 | 714.61 |
| 40 | 695.33 |
| 41 | 684.24 |
| 42 | 619.63 |
| 43 | 604.69 |
| 44 | 495.73 |
| 45 | 488.01 |
| 46 | 454.74 |
| 47 | 431.12 |
| 48 | 422.92 |
| 49 | 413.76 |
| 50 | 393.03 |
| 51 | 369.41 |
| 52 | 350.12 |
| 53 | 323.12 |
| 54 | 299.01 |
| 55 | 270.57 |
| 56 | 240.19 |
| 57 | 205.96 |
| 58 | 160.16 |
| 59 | 133.64 |
| 60 | 114.84 |
| 61 | 82.53 |
| 62 | 78.68 |
| 63 | 70.48 |
| 64 | 54.57 |

The present invention comprises pharmaceutical compositions and formulations comprising any one of the crystalline forms of funapide, the amorphous form of funapide or the crystalline form of the racemic mixture of the present invention and one or more pharmaceutically acceptable excipients. Typically, the pharmaceutical composition is a solid composition and the funapide retains its solid state form therein.

The pharmaceutical compositions of the invention can be prepared by methods similar to those disclosed in PCT Published Patent Application WO 2011/047174 or by methods similar to those disclosed in PCT Published Patent Application No. WO 2013/154712 or by methods similar to those disclosed in PCT Published Patent Application No. WO 2011/106729.

The above crystalline forms of funapide and the racemic mixture and the amorphous form of funapide of the present invention can also be used as a medicament.

The present invention further encompasses 1) the use of the above-described crystalline forms or amorphous form of funapide or the crystalline form of the racemic mixture in the manufacture of a pharmaceutical composition, and 2) a method of treating a subject suffering from sodium channel-mediated diseases and conditions, such as pain, or otherwise in need of the treatment, comprising administration of an effective amount of a pharmaceutical composition comprising any one of the above crystalline forms or amorphous form of funapide described herein.

The use of the above crystalline forms or amorphous form of funapide or the crystalline form of the racemic mixture and pharmaceutical compositions comprising same can be used in treating the diseases and conditions as described in PCT Published Patent Application No. WO 2011/002708.

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to limit its scope in any way.

The funapide used herein to prepare the crystalline forms of funapide disclosed herein was prepared according to the methods disclosed in PCT Published Patent Application No. WO 2011/047174 and/or by the methods disclosed in PCT Published Patent Application No. WO 2013/154712.

Analysis Methods
XRPD—X-Ray Powder Diffraction

X-ray powder diffraction (XRPD, also known as powder X-ray diffraction or powder XRD) patterns were recorded on a PANalytical X'Pert Pro diffractometer equipped with an X'celerator detector using Cu Kα radiation at 45 kV and 40 mA. The diffractometer was controlled with PANalytical Data Collector1. All samples were analyzed using algorithms in HighScorePlus2.

Standard Reflection Mode

Kα1 radiation was obtained with a highly oriented crystal (Ge111) incident beam monochromator. A 10 mm beam mask, and fixed (¼°) divergence and anti-scatter (⅛°) slits were inserted on the incident beam side. A 0.04 radian Soller slits and a fixed 5 mm receiving slit were inserted on the diffracted beam side. The X-ray powder pattern scan was collected from ca. 2 to 40° 2θ with a 0.0080° step size and 96.06 sec counting time which resulted in a scan rate of approximately 0.5°/min. The sample was spread on a silicon zero background (ZBG) plate for the measurement. The sample was rotated at 15 revolutions/min on a PANalytical PW3065/12 Spinner. Measurement of the Si reference standard before the data collection resulted in values for 2θ and intensity that were well within the tolerances of $28.0°<2\theta<28.5°$ and significantly greater than the minimum peak height of 150 cps.

Capillary Transmission Mode

Powder XRD patterns were recorded on a PANalytical X Pert Pro diffractometer equipped with an X celerator detector using Cu Kα radiation at 45 kV and 40 mA. An incident beam (Cu W/Si) focusing MPD mirror was used in the incident beam path. Fixed (1/20) divergence and anti-scatter (1/40) slits and 0.01 Sollers were inserted on the incident beam side. A fixed 5.0 mm antiscatter slit and 0.01 Sollers were inserted on the diffracted beam side. If the antiscatter device (PW3094/10) is employed, an additional 2.0 mm slit is positioned 197 mm from the detector. The X-ray powder pattern scan was collected from ca. 2.75 to 40° 2θ with a 0.0080° step size and 101 second counting time which resulted in a scan rate of approximately 0.5°/min. The sample was loaded into a thin walled Kapton capillary and place in a modified transmission holder. The holder is a standard transmission sample ring with added mechanical features that allow for measurement of a spinning capillary.

Variable Temperature (VT) Mode

Variable temperature studies were preformed with an Anton Paar CHC temperature/humidity chamber under computer control. The temperatures were set with Data Collector using an Anton Paar TCU110 temperature control unit.

Kα radiation was obtained with a Nickel filter. A fixed (1/40) divergence and anti-scatter (1/20) slits were inserted on the incident beam side. A fixed 0.10 mm receiving slit was inserted on the diffracted beam side. Soller slits (0.04 radians) were inserted in both the incident and diffracted beam sides. The X-ray powder pattern scan was collected from ca. 2 to 40° 2θ with a 0.0080° step size and 96.06 sec counting time which resulted in a scan rate of approximately 0.5°/min.

For temperature studies, measurements were made with $N_2$ gas flow. The temperatures chosen for study were based on DSC results. Measurements were started after the CHC chamber reached requested temperature. After the requested temperature was reached, the sample was cooled at 35° C./minute and a slow scan was measured at 25° C. This technique avoids "cooking" the sample at higher temperatures. Scans were collected from ca. 3° to 30° or 40° 2θ with a 0.008° step size and 100 sec counting time which resulted in a scan rate of approximately 0.5°/min.

DSC—Differential Scanning Calorimetry

Thermal curves were acquired using a Perkin-Elmer Sapphire DSC unit equipped with an autosampler running Pyris software version 6.0 calibrated with Indium prior to analysis. Solid samples of 1-10 mg were weighed into 20 μL aluminum pin hole sample pans. The DSC cell was then purged with nitrogen and the temperature heated from 0 to 270° C. at 10° C./min. Indium (Tm=156.6° C.; ΔHFus=28.45 J/g) was used for calibration.

FTIR Spectroscopy

Spectra were obtained using a Bruker Tensor 27 with ATR attachment containing a diamond crystal window. The OPUS data collection program (Version 7.0, Bruker) was used to obtain the IR spectrum from 4000 to 400 cm$^{-1}$. A background scan was collected before spectral resolution and averaged.

Raman Spectroscopy

Raman spectra were collected on a Vertex 70 FTIR (Bruker) optical bench equipped with a 1064 nm NdYAG laser and liquid-nitrogen cooled Ge detector with either the RAMII module or the RamanScope. Thirty-two scans were collected in a double-sided acquisition mode at 5 KHz scan velocity with a 5 mm aperture. Data was processed with a phase resolution of 32 cm$^{-1}$, 8× zero-filling and a weak Norton-Beer apodization function. Sample spectra were collected through the glass vial using the RAMII whenever possible. Irregularly shaped samples were analyzed on the RamanScope using a 10×. In that situation, 64 scans were collected with an 1197 mW laser power.

Screening Methods

Slurry Equilibration in Different Solvents

Equilibration at 25° C.

Approximately 20 mg of funapide was equilibrated with ~0.2 mL solvents for at least 48 h at 25±3° C. in 4 mL vials. The resulting mixtures were filtered and the solids air-dried for at least 10 min.

Equilibration at 50° C.

Approximately 40 mg of funapide was equilibrated with ~0.4 mL solvents for at least 24 h at 50° C. in 4 mL vials. The solutions were then filtered and air-dried for at least 10 min.

Cooling Crystallization at 5° C.

Approximately 20 mg of funapide was completely dissolved in 200 μL of solvents at 22-25° C. in 4 mL vials. Care was taken to ensure that there were no visible crystals remaining. The solutions were cooled to 5° C. at a rate of 2° C./min. The precipitates (if present) were collected on a filter and dried.

Evaporation

Slow Evaporation at 5° C.

Approximately 20 mg of funapide were completely dissolved in 200 μL of solvents at 22-25° C. in 4 mL vials. The solutions were cooled to 5° C. at a rate of 2° C./min. Care was taken to ensure there were no visible crystals remaining. While temperature and agitation were maintained, the cover of each vial was loosened to allow slow evaporation of the solvent for at least one day.

Fast Evaporation at 50° C.

Approximately 40 mg of funapide were mixed with 200 μL of solvents at 22-25° C. in 4 mL vials. The solutions were heated to 50° C. as fast as the instrument allowed. Care was taken to ensure there were no visible crystals remaining at this point. With temperature and agitation maintained, each vial was uncovered to allow fast evaporation of the solvent until dryness.

Precipitation by Addition of Anti-Solvent

In 4 mL vials, approximately 20 mg of funapide were completely dissolved in solvents where funapide solubility is high, and then a second solvent, in which funapide is highly insoluble, was added. Samples were withdrawn from the resulting slurry. The samples were filtered to obtain solids.

Examples 1-66

The following Examples 1-66 are the solid state forms of funapide resulting from screening with the different methods described above in varying solvents.

TABLE 5

Equilibration at 25° C. (Examples 1-18)

| Example | Solvent | XRPD |
|---|---|---|
| 1 | Chloroform/2-propanol (1:3) | $A_0$ |
| 2 | 1,4-dioxane/water (1:3) | $A_0$ |
| 3 | Ethyl acetate/2-propanol (1:3) | $A_0$ |
| 4 | 2-propanol | $B_0$ |
| 5 | Acetone/water (1:1 v:v) | $B_0$ |
| 6 | Acetic Acid/water (1:1) | $B_0$ |
| 7 | Chloroform/heptanes (1:3) | $B_0$ |
| 8 | Dichloromethane/heptanes (1:3) | $B_0$ |
| 9 | Dichloromethane/2-propanol (1:3) | $B_0$ |
| 10 | Ethyl acetate/heptanes (1:3) | $B_0$ |
| 11 | Isobutyl alcohol/heptanes (1:3) | $B_0$ |
| 12 | Isopropyl acetate/heptanes (1:3) | $B_0$ |
| 13 | Methyl tert-butyl ether/heptanes (1:3) | $B_0$ |
| 14 | Tetrahydrofuran/heptanes (1:3) | $B_0$ |
| 15 | Toluene/heptanes (1:3) | $B_0$ |
| 16 | N-butyl acetate/heptanes (1:1) | $A_0 + B_0$ |
| 17 | N-butyl acetate/2-propanol (1:3) | $A_0 + B_0$ |
| 18 | Heptane | $A_0 + B_0$ |

TABLE 6

Equilibration at 50° C. (Examples 19-30)

| Example | Solvent | XRPD |
|---|---|---|
| 19 | Heptanes | $A_0$ |
| 20 | Water | $A_0$ |
| 21 | Acetic Acid/water (1:1) | $A_0$ |
| 22 | Acetone/water (1:1) | $A_0$ |
| 23 | n-Butyl acetate/heptanes (1:3) | $A_0$ |
| 24 | Chloroform/heptanes (1:3) | $A_0$ |
| 25 | Chloroform/2-propanol (1:3) | $A_0$ |
| 26 | Ethyl acetate/heptanes (1:3) | $A_0$ |
| 27 | Isobutyl alcohol/heptanes (1:3) | $A_0$ |
| 28 | Isopropyl acetate/heptanes (1:3) | $A_0$ |
| 29 | Methyl tert-butyl ether/heptanes (1:3) | $A_0$ |
| 30 | Toluene/heptanes (1:3) | $A_0$ |

TABLE 7

Cooling Crystallization at 5° C. (Example 31)

| Example | Solvent | XRPD |
|---|---|---|
| 31 | Methyl tert-butyl ether | $A_0$ |

TABLE 8

Slow Evaporation at 5° C. (Examples 32-39)

| Example | Solvent | XRPD |
|---|---|---|
| 32 | Acetone | $A_0$ |
| 33 | N-butyl acetate | $A_0$ |
| 34 | Ethyl acetate | $A_0$ |
| 35 | Isobutyl alcohol | $A_0$ |

TABLE 8-continued

Slow Evaporation at 5° C. (Examples 32-39)

| Example | Solvent | XRPD |
|---|---|---|
| 36 | Isopropyl acetate | $A_0$ |
| 37 | Methyl tert-butyl ether | $A_0$ |
| 38 | Tetrahydrofuran | $A_0$ |
| 39 | Ethyl acetate/heptanes (4:1) | $A_0$ |

TABLE 9

Fast Evaporation at 50° C. (Examples 40-45)

| Example | Solvent | XRPD |
|---|---|---|
| 40 | Acetone | $A_0$ |
| 41 | Dichloromethane | $A_0$ |
| 42 | Isopropyl acetate | $A_0$ |
| 43 | Methyl tert-butyl ether | $A_0$ |
| 44 | Tetrahydrofuran | $A_0$ |
| 45 | Toluene | $A_0$ |

TABLE 10

Anti-Solvent Addition at Room Temperature (Examples 46-66)

| Example | Solvent 1 and solvent 2 | XRPD |
|---|---|---|
| 46 | Acetic Acid/water (1:1) | $A_0$ |
| 47 | Acetone/water (1:1) | $A_0$ |
| 48 | n-Butyl acetate/heptanes (1:3) | $B_0$ |
| 49 | n-Butyl acetate/2-propanol (1:3) | $A_0$ |
| 50 | Chloroform/heptanes (1:3) | $B_0$ |
| 51 | Chloroform/2-propanol (1:3) | $A_0$ |
| 52 | Dichloromethane/heptanes (1:3) | $B_0$ |
| 53 | Dichloromethane/2-propanol (1:3) | $A_0$ |
| 54 | 1,4-dioxane/water (1:3) | $B_0$ |
| 55 | Ethyl acetate/heptanes (1:3) | $B_0$ |
| 56 | Isobutyl alcohol/heptanes (1:3) | $B_0$ |
| 57 | Isopropyl acetate/heptanes (1:3) | $B_0$ |
| 58 | Tetrahydrofuran/heptanes (1:3) | $B_0$ |
| 59 | Toluene/heptanes (1:3) | $A_0$ |
| 60 | Acetic Acid/water (1:1) | $A_0$ |
| 61 | Acetone/water (1:1) | $A_0$ |
| 62 | n-Butyl acetate/heptanes (1:3) | $B_0$ |
| 63 | n-Butyl acetate/2-propanol (1:3) | $A_0$ |
| 64 | Chloroform/heptanes (1:3) | $B_0$ |
| 65 | Chloroform/2-propanol (1:3) | $A_0$ |
| 66 | Dichloromethane/heptanes (1:3) | $B_0$ |

Example 67

Crystallization Process for Form $B_0$ of Funapide

Funapide (1.952 Kg) was dissolved in 7070 mL methanol (3.62 volumes). Full dissolution in the 10 L reactor was obtained at 56° C. (in reactor). When the reactor temperature reached 64° C., 742 mL of water were added dropwise over a period of 65 minutes. At the end of the water addition period a clear solution was still obtained (reactor temperature reached 68° C.). The solution was mixed for 30 minutes. The jacket temperature was cooled from 85° C. to 40° C. over a period of 40 minutes. At the end of this cooling period, temperature in reactor reached 59° C. (jacket temperature was 40° C.) and a white slurry was obtained. The slurry was cooled according to reactor jacket temperature from 40° C. to −5° C. over a period of 5 hours and mixed for additional 11.5 hours. The solid obtained was collected by filtration and washed with cold mixture of methanol and water (908 mL water and 1160 mL methanol). The white solid was dried in a vacuum oven at 50° C. for 43 hours to obtain a dry solid. Yield: 1831 g (93.8% of theory).

The material was analyzed by XRPD, showing a Form $B_0$ pattern. The DSC of the sample had thermal events at 106.6° C., which is consistent with the typical Form $B_0$.

Example 68

Preparation of Amorphous Form of Funapide

A. The amorphous form of funapide was generated by melting Form $A_0$ of funapide in a dry $N_2$ atmosphere optionally using the VT stage on the XRPD unit. The sample was heated to 140° C. and then cooled to room temperature and crushed. No decomposition was observed. The sample was confirmed to be the amorphous form of funapide by XRPD.

B. Alternatively, Form $B_0$ of funapide may be melted in the same manner to produce the amorphous form of funapide.

Example 69

Solid State Characterization of Racemic Mixture

A racemic mixture comprising funapide (as Form $A_0$ of funapide) and its corresponding (R)-enantiomer was studied to determine if the racemic mixture was a racemic compound or a racemic conglomerate.

FIG. 11 shows a characteristic X-ray powder diffractogram of the racemic mixture. FIG. 12 shows the Raman shift spectrum for the racemic mixture.

Figure 13:
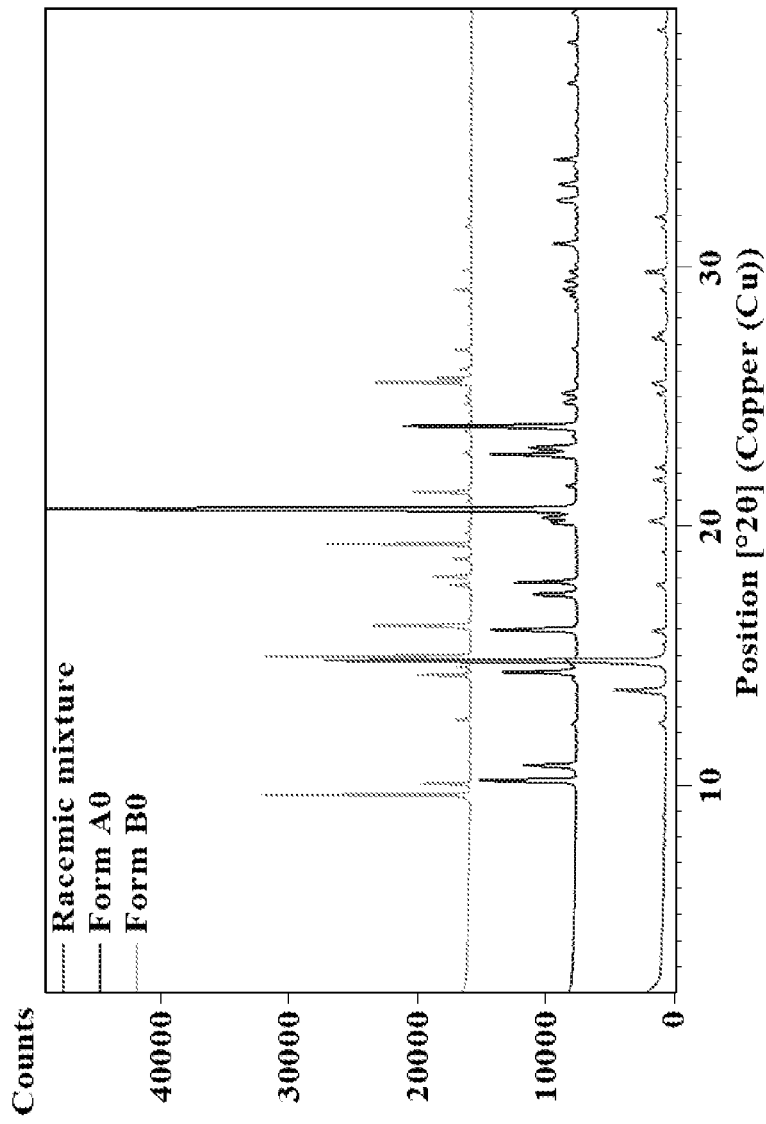
FIG. 13 shows an overlay of the X-ray powder diffractograms of the racemic mixture, Form $A_0$ of funapide and Form $B_0$ of funapide.
Figure 14:
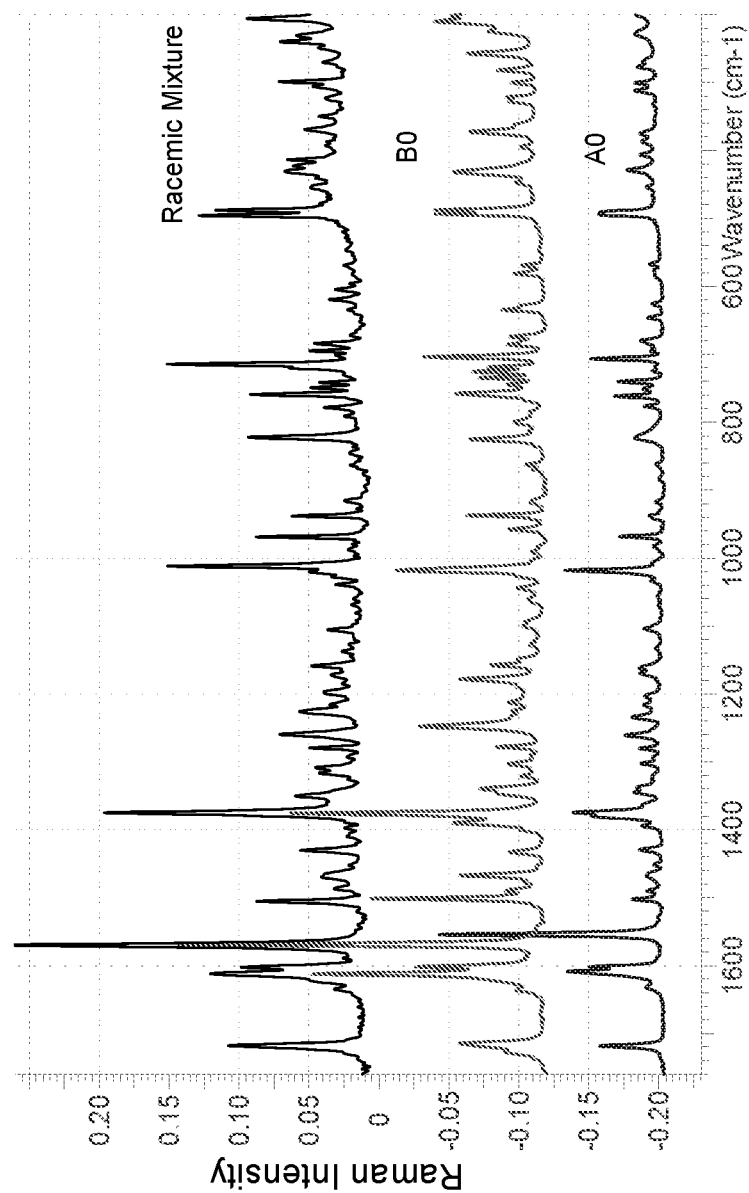
FIG. 14 shows an overlay of the Raman shift spectrums of the racemic mixture, Form $A_0$ and Form $B_0$.

FIG. 13 shows an overlay of the X-ray power diffractograms of the racemic mixture, Form $A_0$ of funapide and Form $B_0$ of funapide. FIG. 14 shows an overlay of the Raman shift spectrum of the racemic mixture, Form $A_0$ and Form $B_0$.

The XRPD pattern and melting point of the racemic mixture are drastically different from that of Form $A_0$ and Form $B_0$ (140° C. vs. 110° C. of Form $A_0$ and 104° C. of Form $B_0$). Shifts of some Raman peaks of the racemic mixture were also noticeable when compared to those of Form $A_0$ or Form $B_0$.

To identify the nature of the racemic mixture, a binary phase diagram from DSC's of mixtures of the racemic mixture and Form $A_0$ was constructed based on experimental results and theoretical predication. A good agreement was observed between the experimental results and theoretical predications. The typical binary phase diagram of a racemic compound confirmed that the racemic mixture is a racemic compound (instead of a racemic conglomerate).

An overlay of 6 DSC thermographs of the racemic mixture, Form $A_0$ and different mixtures of the racemic mixture and Form $A_0$ showed that Form $A_0$ and the racemic mixture both have one sharp peak which corresponds to the melting of Form $A_0$ and the racemic mixture. The mixtures of the racemic mixture and Form $A_0$, two endothermic peaks; a eutectic fusion (with its onset defined as $T_E$) and a pure species melting (its max as $T_f$) were observed.

The crystal structure of the racemic mixture was resolved. There was one molecule in the asymmetric unit and there were four pairs of enantiomers packed in one unit cell. Furthermore, the molecule conformed to the "U-shape" of Form $B_0$ (rotation along the N—$CH_2$ bond in funapide gives either a "Chair-shape", which conforms with Form $A_0$, or a "U-shape", which conforms with Form $B_0$).

The crystal structure determination of the racemic mixture provides definitive evidence that the racemic mixture is a racemic compound rather than a conglomerate.

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A crystalline form of funapide, designated as Form $B_0$, characterized by one or more of the following: a powder X-ray diffraction pattern having peaks at 9.61°, 10.03°, 14.95°, 19.28°, and 21.30° θ±0.2° θ; a powder X-ray diffraction pattern substantially as depicted in FIG. 5; and any combination of these data.

2. The crystalline form of funapide of claim 1, characterized by a powder X-ray diffraction pattern having peaks at 9.61°, 10.03°, 14.95°, 19.28°, and 21.30° θ±0.2° θ, further characterized by an additional one, two, three, four or five powder X-ray diffraction pattern peaks selected from 12.51°, 16.14°, 18.03°, 18.72°, and 25.50° θ±0.2° θ.

3. The crystalline form funapide of claim 1 or 2, further characterized by one or more of the following: a DSC thermogram substantially as depicted in FIG. 6; an endothermic onset at 103° C. and a peak max at 105° C., or combinations thereof.

4. A pharmaceutical composition comprising the crystalline form of funapide according to claim 1.

5. A pharmaceutical formulation comprising the crystalline form of funapide according claim 1 and at least one pharmaceutically acceptable excipient.

6. A pharmaceutical formulation comprising the pharmaceutical composition of claim 4 and at least one pharmaceutically acceptable excipient.

7. A method of treating a subject suffering from sodium channel-mediated diseases and conditions, wherein the method comprises administering to the subject a pharmaceutical composition according to claim 4.

8. A method of treating a subject suffering from sodium channel-mediated diseases and conditions, wherein the method comprises administering to the subject the pharmaceutical formulation according to claim 6.

9. A method of treating a subject suffering from sodium channel-mediated diseases and conditions, comprising administering to the subject a therapeutically effective amount of the crystalline form of funapide according to claim 1.

10. A method of preparing a pharmaceutical composition comprising combining the crystalline form of funapide according to claim 1 with a one or more pharmaceutically acceptable excipients.

11. A method of preparing a crystalline form of funapide designated as Form $B_0$, wherein the method comprises:
(a) dissolving funapide in an appropriate amount of methanol under suitable conditions to form a solution;
(b) adding an appropriate amount of water to the solution under suitable conditions to form a slurry;
(c) filtering the slurry under suitable conditions to obtain a solid;

(d) washing the solid with a mixture of methanol and water under suitable conditions; and
(e) drying the solid under suitable conditions to obtain the crystalline form of funapide designated as Form $B_0$.

* * * * *